(12) United States Patent
Gelfand et al.

(10) Patent No.: US 6,468,241 B1
(45) Date of Patent: Oct. 22, 2002

(54) ARTIFICIAL KIDNEY SET WITH ELECTRONIC KEY

(75) Inventors: Mark Gelfand, New York, NY (US); John J. O'Mahony, Hackensack, NJ (US)

(73) Assignee: CHF Solutions, Inc., New York, NY (US)

(*) Notice: Subject to any disclaimer, the term of this patent is extended or adjusted under 35 U.S.C. 154(b) by 2 days.

(21) Appl. No.: 09/696,642

(22) Filed: Oct. 26, 2000

(51) Int. Cl.[7] .................................................. A61M 1/34
(52) U.S. Cl. ...................... 604/6.09; 210/646; 604/6.11
(58) Field of Search .......................... 210/646; 604/6.09, 604/6.11

(56) References Cited

U.S. PATENT DOCUMENTS

| | | | |
|---|---|---|---|
| 4,086,924 A | | 5/1978 | Latham, Jr. |
| 4,379,452 A | * | 4/1983 | DeVries ...................... 604/6.11 |
| 4,464,164 A | * | 8/1984 | Troutner et al. ............ 604/6.11 |
| 4,464,172 A | | 8/1984 | Lichtenstein |
| 4,657,529 A | | 4/1987 | Prince et al. |
| 4,897,789 A | | 1/1990 | King et al. |
| 4,936,980 A | | 6/1990 | Yoshimichi et al. |
| 5,114,580 A | | 5/1992 | Ahmad et al. |
| 5,312,550 A | | 5/1994 | Hester |
| 5,536,237 A | | 7/1996 | Prince et al. |
| 5,685,989 A | | 11/1997 | Krivitski et al. |
| 5,707,086 A | | 1/1998 | Treu et al. |
| 5,725,776 A | | 3/1998 | Kenley et al. |
| 5,906,589 A | | 5/1999 | Gordon et al. |
| 5,910,252 A | | 6/1999 | Truitt et al. |
| 5,920,054 A | | 7/1999 | Uber |
| 6,090,048 A | | 7/2000 | Hertz et al. |

FOREIGN PATENT DOCUMENTS

EP 0771 569 5/1997
WO WO 94/10921 11/1993

OTHER PUBLICATIONS

Sasse et al., U.S. patent application Publication No. 2001/0020148, Pub. Date: Sep. 2001.

Lauer, A. et al, "Continuous Arteriovenous Hemofiltration in the Critically Ill Patient, Clinical Use and Operational Characteristics," Annals of Internal Medicine 99:455–460 (1983).

Verbanck, J. et al, "Pure Ultrafiltration by Repeated Puncture of a Peripheral Arm–Vein as Treatment of Refratory Edema", The International Journal of Artificial Organs, vol. 3, No. 6 (1980), pp 342–343.

Silverstein et al, "Treatment of Severe Fluid Overload by Ultrafiltration," The New England Journal of Medicine, vol. 291, No. 15, Oct. 10, 1974, pp. 747–751.

(List continued on next page.)

Primary Examiner—Gerald A. Michalsky
(74) Attorney, Agent, or Firm—Nixon & Vanderhye, P.C.

(57) ABSTRACT

An integrated disposable set for dialysis or ultrafiltration treatment of blood is disclosed that includes a memory "key" chip. The key contains information relating to the set, including calibration for sensors, model and date of manufacture and a proprietary secret code to prevent unauthorized duplication of a circuit. The key is activated when treatment of a patient begins to prevent reuse of the set and a delay in use of the set that is too long. Patient data and operational information can be stored in the key during treatment. The key can be returned to the manufacturer or entered into hospital database for analysis. The key is preferably an EEPROM chip that can be embedded in an integral circuit sensor or a separate plug in device, such as a code card.

11 Claims, 4 Drawing Sheets

OTHER PUBLICATIONS

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166–173.

Civati G. et al, "Haemofiltration Without Substitution Fluid," Proc. EDTA–ERA, vol. 21 (1984), pp. 441–446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, $4^{th}$ Ed., (1996) pp. 391–397.

Gupta, B.B. et al, "High Shear Rate Hemofiltration: Influence of Fiber Dimensions and Shear Rates," Artificial Organs, International Society for Artificial Organs, vol. 13(2) (1989), pp. 97–102.

Rimondini, A. et al, "Hemofiltration as Short–Term Treatment for Refactory Congestive Heart Failure," The American Journal of Medicine, vol. 83, Jul. 1987, pp 43–48.

Donato, L. et al, "Treatment of End–Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384–390.

Chen, Y. et al, "Direct Peripheral Venopuncture: Another New Choice of Temporary Vascular Access", Renal Failure, 22(3), 369–377 (2000).

* cited by examiner

ARTIFICIAL KIDNEY SET WITH ELECTRONIC KEY

FIELD OF THE INVENTION

This invention relates to the extracorporeal treatment of blood, and more particularly to the Renal Replacement Therapy or Artificial Kidney.

BACKGROUND OF THE INVENTION

1. Mechanical Fluid Removal Therapies

Different modalities of Continuous Renal Replacement Therapy (CRRT) have been used to treat patients suffering from excess fluid overload and acute renal failure. In the acute setting, CRRT has been performed previously using standard methods of hemodialysis and continuous arterio-venous hemofiltration (CAVH). More recently, continuous veno-venous hemofiltration (CVVH) has been used to reduce the complications associated with such issues as hemodynamic instability and need for arterial access.

Renal replacement therapy performs two primary functions: ultrafiltration (removal of water from blood plasma), and solute clearance (removal of different molecular weight substances from blood plasma). The filter, also called hemofilter or "dialyzer", can be set up to perform either or both of these functions simultaneously, with or without fluid replacement, accounting for the various modes of renal replacement therapy. "Clearance" is the term used to describe the removal of substances, both normal and waste product, from the blood.

Ultrafiltration is the convective transfer of fluid out of the plasma compartment through pores in the membrane. The pores filter electrolytes and small and middle sized molecules (up to 20,000 to 30,000 daltons) from the blood plasma. The ultrafiltrate output from the filtration pores is similar to plasma, but without the plasma proteins or cellular components. Importantly, since the concentration of small solutes is the same in the ultrafiltrate as in the plasma, no clearance is obtained, but fluid volume is removed.

Dialysis is the diffusive transfer of small solutes out of a blood plasma compartment by diffusion across the membrane itself. It occurs as a result of a concentration gradient, with diffusion occurring from the compartment with higher concentration (typically the blood compartment) to the compartment with lower concentration (typically the dialysate compartment). Since the concentration of solutes in the plasma decreases, clearance is obtained, but fluid may not be removed. However, ultrafiltration can be combined with dialysis.

Hemofiltration is the combination of ultrafiltration, and fluid replacement typically in much larger volumes than needed for fluid control. The replacement fluid contains electrolytes, but not other small molecules. Since the net effect of replacing fluid without small solutes and ultrafiltration of fluid with small solutes results in net removal of small solutes, clearance is obtained.

2. Limitations of Existing Devices for Ultrafiltration

Dialysis Machines historically used sets of disposables that can be assembled of various parts from different manufacturers. This allowed flexibility in use, but had certain disadvantages. Joints between parts will spring leaks, allowing ingress of air and facilitating clotting. A high degree of skill was required from users to assemble tubes, connectors, filters and accessories and then load them correctly into pumps, bubble detectors, pressure sensors and other interface elements of a dialysis machine. While in the setting of a chronic dialysis center, such practice was acceptable. In the acute setting, such as an Intensive Care Unit (ICU) of a hospital, it became an impediment.

This, among other factors, led to under utilization of mechanical fluid removal in the ICU of a hospital in the past. In the U.S., only recently was the sophisticated apparatus "Prisma" from Hospal-Gambro released. This device uses an integrated set where tubing, filter and accessories are all bonded together in the right order and no assembly is required. The filter, sensor interfaces and the four dedicated pump segments (for blood, dialysate, replacement solution and effluent) are also mounted on a flat plastic cartridge to simplify the loading of pumps. The manufacturer advertises the Prisma machine as "an integrated system for continuous fluid management and automated renal replacement therapy blood."

Recent changes in the dialysis technology introduced microprocessors, computer graphics interfaces and sophisticated control algorithms. The new generation of controls allows more accurate and safe ultrafiltration. The bases for the advances controls are the sensors. Dialysis equipment uses a variety of sensors that interface with the fluid flow. The sensors include standard configuration pressure sensors, blood leak (typically photometric) sensors and air detection (typically ultrasonic) sensors. Lately, some manufacturers have introduced flow sensors, conductivity sensors, and blood hematocrit sensors.

In all existing dialysis, ultrafiltration and hemofiltration equipment sensors are part of capital equipment. The single use dialysis sets, integrated or not, only include plastic parts with no built in intelligence. Properties of the plastic material as well as mounting conditions contribute to the uncertainty of measurement. For example a 1% accurate pressure sensor can be used to measure blood pressure in the blood return line. Pressure is transmitted from blood through the silicon diaphragm that is a part of the disposable set. Owing to manufacturing methods and properties of the material, the elasticity of the diaphragm has inherent variability of 10%. As a result, practical accuracy of the sensor is dramatically reduced. The sensor to media interface also reduces other performance parameters, such as frequency response, resolution, and stability.

Another noted limitation of the existing dialysis sets is the lack of traceability associated with the single use set. In some countries, dialyzers (the most expansive component) are reused, but sets of tubing are always disposable. All disposable sets have serial numbers and limited shelf life. It is the responsibility of the user to ensure that the serial number of the set is recorded, and that the set is not reused or kept out of the package and on the machine longer than is safe. Yet another limitation of the existing single use dialysis set technology is that it can be easily replicated by "after market" manufacturers after the original equipment manufacturer has invested in development. This way, dialysis equipment manufacturers have no means of preventing users from using sets that are made by competitors. There is also an associated danger of an incompatible or partially compatible set being used without the knowledge of the manufacturer of the capital equipment.

Digital technologies allow easy storage of significant amounts of digital information in relatively inexpensive miniature ROM (Read Only Memory) chips. In recent years the medical disposables technologies are making increasing use of them. There have been several devices where the disposable component of a medical device has an integral or added "memory" component. For example, U.S. Pat. No. 5,720,293 discloses a diagnostic catheter with a memory chip where calibration, patient and serial number information can be stored. Camino Neural Care of San Diego, Calif. manufactures a disposable intra cranial pressure catheter for use in neurosurgery that comes with an individually programmed memory "key" that contains calibration information for the pressure sensor. None of the aforementioned devices addresses specific needs of an advanced dialysis set.

The present invention is a new and improved integrated disposable set with a memory device for storing useful information used in a dialysis or ultrafiltration set to improve accuracy of sensors, prevent reuse and incorrect use and to protect the set rom replication and selling by competitor.

SUMMARY OF THE INVENTION

It is an object of the present invention to address the needs of fluid removal and dialysis in the acute and emergency settings. It is another object of the present invention to eliminate significant limitations of existing fluid removal and dialysis devices.

The present invention is directed to a memory device that is used with a disposable ultrafiltration set for dialysis or fluid removal in fluid overloaded patients. The memory device or "key" is preferably an EEPROM that is embedded in a blood circuit sensor used with the ultrafiltration set or a separate key code card that is plugged into the control panel of the set.

The key can contain information about the manufacture and/or use of the disposable ultrafiltration set, including:

Set Model Number;
Serial number;
Encoded Date of manufacture;
Encoded Expiration date of the set;
Proprietary secret code to prevent unauthorized duplication of a circuit;
Calibration coefficients for single use pressure sensors that are the part of the set;
Calibration coefficients for single use blood optometric leak detector that is the part of the set;
Calibration coefficients for the single use optical oximery sensor (SvO2) that is the part of the set; and/or
Encoded checksum of above data.

Patient data and operational information can be stored in the key during treatment.

The key can also store information written into the key relating to treatment of a patient:

Date and time when the circuit was mounted on the machine;
Machine serial number and model number;
Machine CPU software revision;
Machine hardware revision;
Date and time when the treatment started;
Duration of treatment;
Treatment modality (SCUF, CVVH, CVVHD etc.);
Alarms;
User actions;
User settings such as blood flow, fluid removal rate;
Actual sensor readings such as circuit pressures, blood and other fluid pump flows, oxygen and other gas contents of blood, hematocrit, venous blood pressure when the pump is stopped;
Total amount of fluid removed per treatment;
Date and time when the circuit was dismounted; and
Battery operation.

Preferably the key is returnable to the manufacturer or usable by a hospitable so that information stored in the key can be entered into databases usable for various objectives.

BRIEF DESCRIPTION OF THE DRAWINGS

A preferred embodiment and best mode of the invention is illustrated in the attached drawings that are described as follows.

DESCRIPTION OF THE PREFERRED EMBODIMENT

The present invention is a memory device that is used with a single use disposable set for dialysis or ultrafiltration of blood to treat fluid overload in patients in a on-ICU setting. The disposable ultrafiltration set is disclosed in commonly-owned U.S. patent application Ser. No. 09/660, 195, filed Sep. 12, 2000, which application is incorporated herein by reference. The ultrafiltration set is mountable on a console equipped with two pumps (for blood and ultrafiltrate). The set contains a disposable circuit with an integral filter and three integrated pressure sensors. Unlike common dialysis disposables that come in separate pouches and need to be assembled, the disposable circuit comes in one organized tray similar to ones used by interventional cardiologists. Inside the tray are all the components that are needed to treat a single patient. The memory key of the present invention is tethered to the disposable circuit and sealed in the tray. A brief description of the disposable set and the console on which it is mounted follows.

Figure 1:
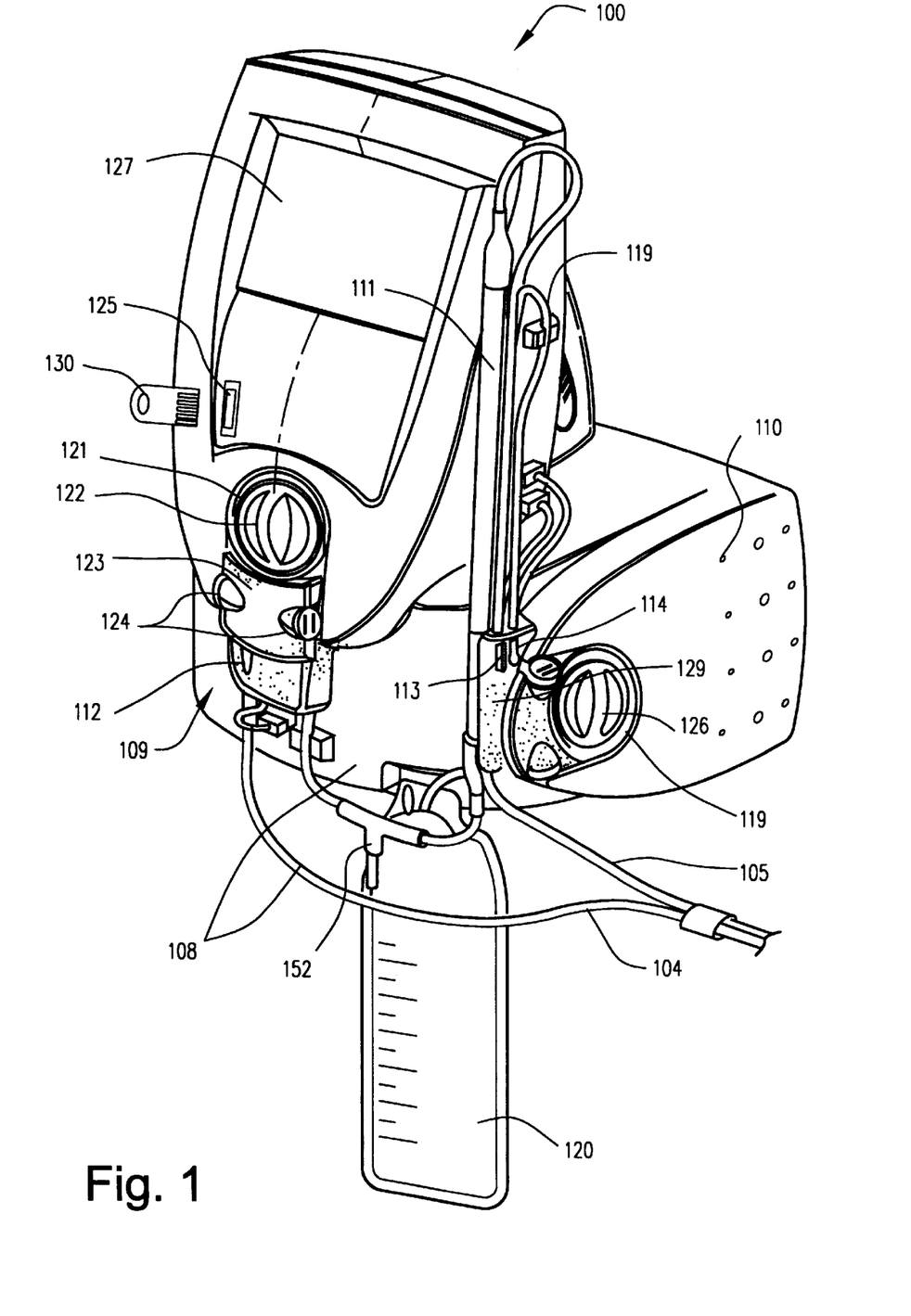
FIG. 1 is a perspective view of an intravenous blood ultrafiltration system using a disposable blood circuit cartridge with an integrated pressure sensor.
Figure 2:
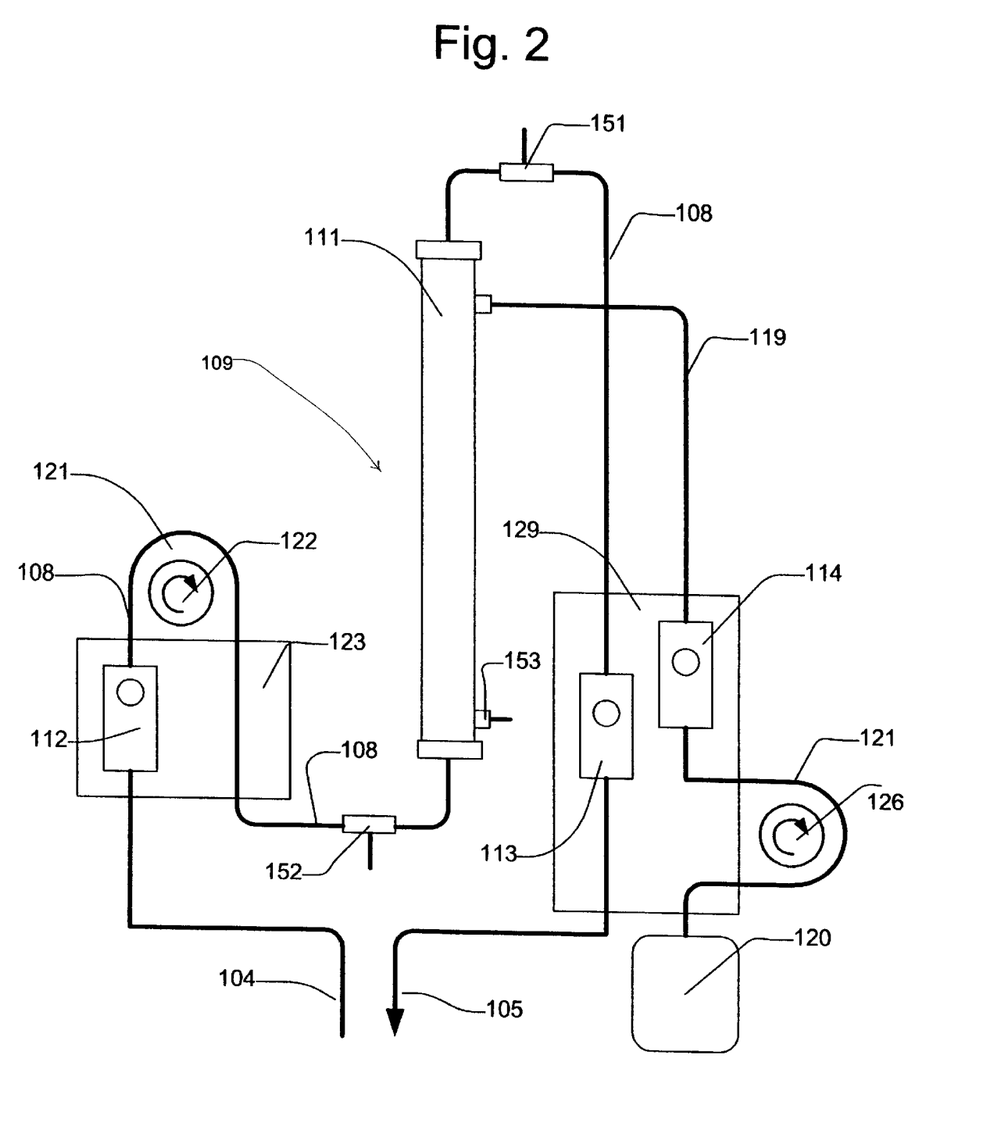
FIG. 2 is a schematic diagram showing a fluid path of blood and removed fluids for the blood circuit cartridge used with the blood ultrafiltration system shown in FIG. 1.

FIG. 1 shows an intravenous blood ultrafiltration system 100 for treating a patient (not shown) suffering from fluid overload. To initiate ultrafiltration treatment, two standard 18G IV needles (not shown) are introduced into suitable peripheral veins (not shown) for the withdrawal and return of the blood. The needles are attached to a withdrawal tubing 104 and a return tubing 105, and secured to skin with attachments, such as adhesive strips (not shown). The withdrawal and return tubing, 104 and 105, forms portions of a continuous blood fluid passage 108 that extends through a disposable blood circuit cartridge 109 (FIG. 2). The disposable blood circuit cartridge 109 is attached to a pumping console 110.

Tubing sections similar to the blood tubing 104 leading from and blood tubing 105 leading to the patient extend through cartridge 109 and form additional links in the blood fluid passage 108. These tubing links are coupled to a blood filter 111 and pressure sensors 112, 113, that are contiguous with the tubing and form sections of the blood fluid passage 108. In other embodiments it can be envisioned that the blood filter 111 is supplied separately and can be connected to the cartridge by the operator before treatment.

The filtrate disposable blood circuit cartridge 109 is supplied separate from the console and packaged in a sterile package. The cartridge is intended to be used for one single treatment, and not to be reused. The cartridge is inserted into the pump console 110 by threading the tubing loops 121 in the blood passage 108, and ultrafiltrate discharge tubing 119 over the rims of roller pumps 122 and 126, respectively. As pumps 122 rotate, they slidably engage the tubing and force blood and ultrafiltrate-fluids to move through the cartridge fluid passages. Microprocessor pump drivers (not shown) control the flow rate of the blood and ultrafiltrate through the cartridge. The pump drivers are part of console 110 and are controlled by a microprocessor controller 128 (FIG. 3) within pump console 110. Electronic key 130 is supplied with the circuit in the same sterile package and inserted into the slot 125 in console 110 prior to treatment.

The tubing of the blood circuit cartridge 109 may be mounted in a molded-plastic housing 123 that fits into a recess in the surface of console 110 and snaps into console 110 with latches 124. A blood withdrawal pressure sensor 112 is mounted to an inside surface of the cartridge housing 123. A pressure sensor 113 for the blood return tube 105 and an ultrafiltrate pressure sensor 114 are mounted to an inside surface of the second cartridge housing 129. Blood pressure sensors 112 and 113 and ultrafiltrate pressure sensor 114 include transducers that convert pressures into electrical signals carried by signal wires 131 that are connected to microprocessor controller 128 in console 110.

In the preferred embodiment of the invention, sensors 112, 113 and 114 are MPX2300D sensors manufactured by Motorola. Filter 111 in the preferred embodiment is a custom-made filter made by Minntech of Minnesota. The filter uses polysulfone hollow fiber available from Minntech or Fersenius of Germany. Pump console 110 in the preferred embodiment is manufactured by Intellicardia.

FIG. 2 is a schematic diagram of the blood and filtrate flow through the ultrafiltration system 100. The system symbolically depicted in the FIG. 2 is designed primarily to perform SCUF (Slow Continuous Ultrafiltration) but can be easily converted for other RRT (Renal Replacement Therapy) modalities. The second hemofilter port 153 is plugged for SCUF. If dialysis is desired, a source of dialysate fluid can be connected to this port. Dialysis fluid will circulate through the filter casing and interface with blood through the hollow fiber membrane. This way clearance can be obtained via the diffusion of solute. For this mode, dialysate may need to circulate in the direction opposite to blood. This can be achieved by reversing the pump 126.

Alternatively access port 152 in the circuit tubing 108 can be used to infuse the replacement solution. Ultrafiltration rate can be increased proportionally by speeding up the pump 122. This way clearance can be obtained by convective transport of solute with ultrafiltrate. Similarly, the post-filter port 151 can be used to infuse the replacement solution if desired. With these simple additions well known in the field of RRT, the described apparatus can be used to perform dialysis and hemofiltration.

Regardless of the RRT modality desired, the basic principles of the apparatus design remain the same. Blood that is withdrawn from the patient flows into the withdrawal tubing 104 and enters the blood passage 108 of the cartridge 123. Blood travels inside the hollow fibers through the filter 111 and is returned to the patient via the return tube 105. Prior to return, blood enters the pressure sensor 113 mounted on cartridge 129. Ultrafiltrate, effluent or dialysis solution passes through the filter casing surrounding the blood filled hollow fibers. Pump 122 generates the flow. Pump segment tubing loops 121 are attached to cartridges 123 and 129 to assist loading of pumps and prevent tubes from kinking. In the preferred embodiment, ultrafiltrate line pressure sensor 114 is integrated into the same cartridge as the blood return sensor 113. Pressure sensors 112, 113 are integral to the blood passage 108 in the Cartridges 123 and 129. These sensors are disposed in blood passage 108, such that a diaphragm of the sensor, which is the device that is in fluid contact with the load and directly responds to the blood pressure, is adjacent the blood passage. The diaphragm does not form stagnant areas in the passage. Similarly, pressure sensor 114 (which also includes a diaphragm in fluid contact with the filtered fluid) for the ultrafiltrate is integrally formed in the filtrate tubing 119 between the filter 111 and the ultrafiltration bag 120. Pressure sensors 112, 113 and 114 are included in the disposable cartridge and are intended for one-time use. These pressure sensors each have a generally straight and hollow fluid passage that is coupled to the blood or filtrate tubing in the cartridge. The passages in the sensors are contiguous with the blood and ultrafiltrate passage of the cartridge.

The fluid flow passage in each sensor includes a peripheral wall, a pressure sensing diaphragm that is relatively small compared to the passage. As blood or ultrafiltrate flows across the diaphragm, the pressure of the flow displaces the diaphragm. This diaphragm displacement is converted by a mechanical-to-electrical transducer in the sensor to an electrical signal, e.g., a voltage level, that is indicative of the pressure of the flow. The electrical signal is output by the sensor to the pump console 110 through an electrical signal line, e.g., a wire 131. A microprocessor controller 128 in console 110 receives the pressure signals via the lines 131 and determines the pressure level of the blood or ultrafiltrate in the blood or ultrafiltrate passage in which the associated sensor is positioned.

Preferably, the memory device of the present is a serial EEPROM. The memory device can be integrated into one of the set components that has an electric connection to the console such as a pressure, blood leak, blood oxygen saturation, blood hematocrit or other sensor. Alternatively, the memory device can be a separate device, such as a key or a card, that is inserted into a slot on the faceplate of the machine. Such a device is available off shelf from Datakey, Inc., a leading provider of token-based systems and technology used by worldwide customers to record, store and transmit electronic information. Datakey products, such as "code keys" and "smart cards", are inexpensive, tested, and made in robust packages that can be sterilized and packaged together with the disposable ultrafiltration set. These products also include build in encryption and encoding that allow secrecy desired by the set manufacturer and the protection of a patient's privacy.

Figure 3:
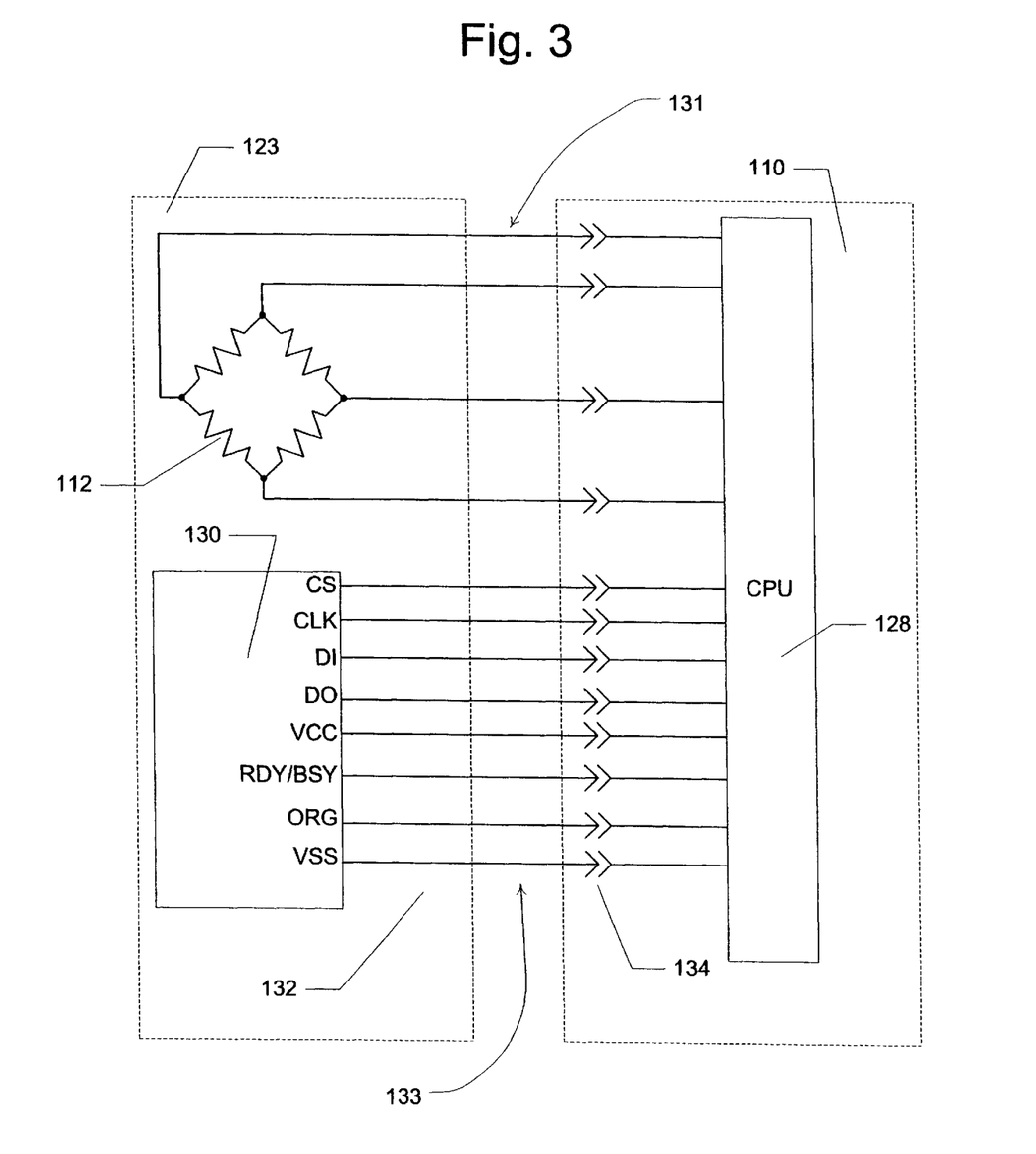
FIG. 3 is a schematic of an integrated pressure sensor and an EEPROM device.

FIG. 3 illustrates one preferred embodiment of the memory device 130 used in the present invention. Memory device 130 is a code key ROM that is either integrated into the housing 123 of the pressure sensor 112, integrated into housing 129 of pressure sensors 113 and 114, or be a separate device which plugs into slot 125 in the faceplate 127 of the ultrafiltering device. Pressure sensors 112, 113 and 114 are conventional bridge type strain gauge devices.

The Code key 130 contains a serial EEPROM (FIG. 4) with the serial number, date of manufacture and other relevant information stored in the device. The preferred embodiment of the code key is a SlimLine Data Carrier from Datakey of Minnesota. The key is an economical, low-cost token with 1K, 4K, and 16K-bit serial memories.

Each SlimLine token contains a serial I/O, read/write memory in either Microwire™ (LCS) or I2C™ (SDD) that holds more information than common magnetic strip cards. Data stored in the device can be read, written, and erased via a simple interface to host hardware with which the device is used. The SlimLine tokens can be programmed directly by the host's microprocessor (e.g., microprocessor controller 128) or accessed through a conventional RS232 reader/writer device. The key is nonvolatile and retains data for 10 years. Importantly, the key is sealed and rugged and can withstand sterilization with the rest of the patient circuit.

Code key 130's serial EEPROM has following inputs and outputs:
CS—chip select
CLK—clock input
DI—data input
DO—data output
VCC—supply voltage 5 VDC
VSS—ground
ORG—organization of the memory array (64×16 or 128× 8)
RDY/BSY—ready or busy signal Referring, by way of example, to pressure sensor 112 shown in FIG. 3, both pressure sensor 112 and EEPROM device 130's wires 132 and 132, respectively, are bundled into the same cable 133. The plug in connector 134 is located on the front panel of the console 110. Signals from both the sensor 112 and the code key 130 are in electronic communication with the microprocessor controller 128 via standard A/D and digital I/O means.

Figure 4:
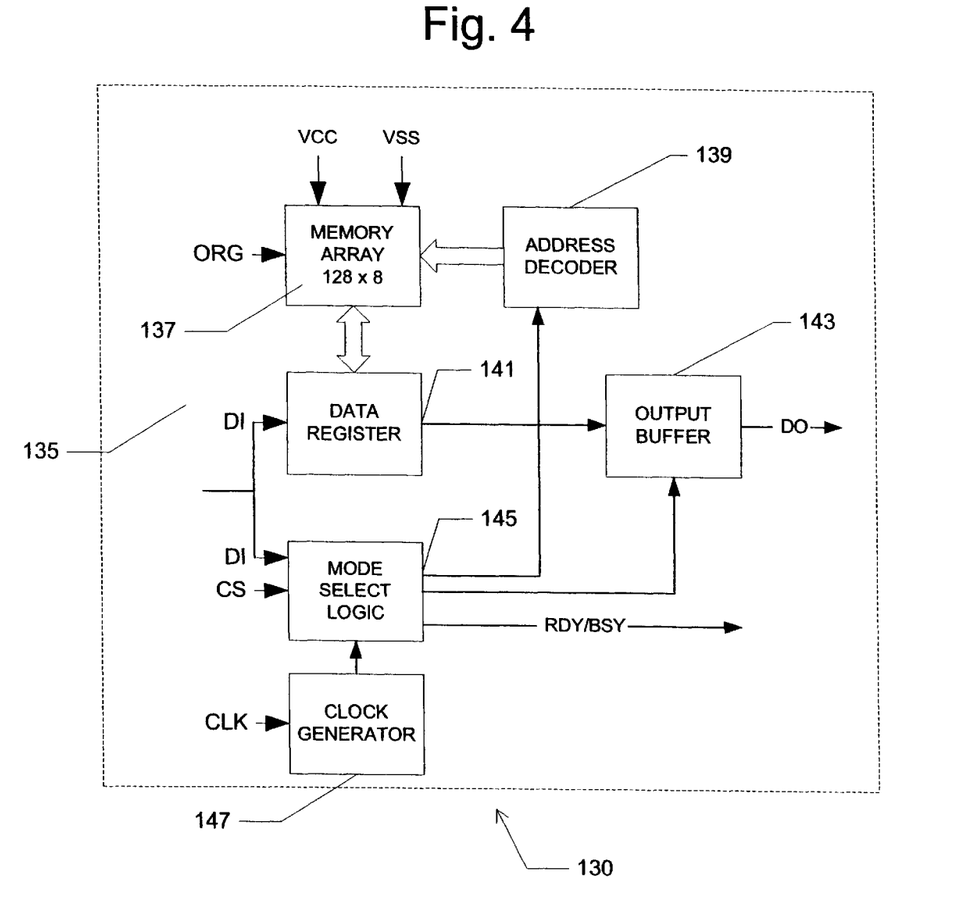
FIG. 4 is a block diagram of the preferred embodiment of the EEPROM device of the present invention.

FIG. 4 shows EEPROM device 130 that is used with the preferred embodiment of the invention. The device is preferably an 8 pin DIP chip 135.

Internally it consists of a memory array 137, address decoder 139, data register 141, output buffer 143, mode select logic 145 and the clock generator 147.

In the initial release of the ultrafiltration set, the code key 130 is programmed with the following information at the factory.:
Calibrations: Pressure transducer gains and offsets. 3 offsets+3 gains (Total 6–16 bit words);
Date of manufacture (1–16 bit word);
Number generated on Key code 130 that fits with a proprietary algorithm. If the number does not compute, key 130 does not allow the use of the disposable circuit. Set forth below is the algorithm used with the preferred embodiment of the invention:
CODE=ABCDEFGH(1–16 bit word)
The code is generated as follows A, B, C, H are random integer numbers between 1 and 9. ((A−B−B)−C−H)=EFG
If (((A−B−B)−C−H)=EFG) key is accepted, else it is rejected.

During operation, the ultrafiltration circuit 109 is connected to console 110. Console 110 will not proceed to priming or treatment of the circuit 109 until a) the memory key 130 is connected to microprocessor controller 128 and b) the memory code is successfully read and analyzed by microprocessor controller 128. When the key 130 is connected, certain data is read into microprocessor controller 128's memory and analyzed. The date and time of 130's key connection is written to key 130 when console 110 enters an operating mode that affects the life of disposable circuit 109. Thereafter, disposable circuit 109 is initialized. The user has 24 hours to use the circuit for treatment. During operation of the ultrafiltration machine, the key initialization time is periodically compared to the current time. If more than 24 hours have elapsed, treatment will continue but cannot be restarted. Any attempt to start the treatment with the key that has been active for more than 24 hours will result in a warning message to the user.

During treatment, useful information may be collected by microprocessor controller 128 and stored in the key 130. Key 130 can be later shipped back to the manufacturer so that the information can be used to collect valuable statistics or help troubleshoot failures. Alternatively, key 130 can be retained by the medical institution using it as a part of the patient history and the information later transferred to a central database for storage and analysis.

During the operation of disposable circuit 109, the following information is stored in key 130:
1) Settings used+duration of use for each setting (10–2–16 bit words);
2) Last technical 20 alarm codes generated (20–16 bit words);
3) Number of patient alarms generated. Each time one occurs, the counter for that alarm is incremented. (15–16 bit words);
4) Number of minutes the key battery was used+duration of use (up to 10 occurrences) (10–16 bit words);
5) Condition of battery during start up–voltage level. (1–16 bit word);
6) Number of times machined was turned on/off with the same circuit. (1–16 bit word);
7) Number of times manual mode was used. (1–16 bit word);
8) Number of times run mode was used. (1–16 bit word);
9) Number of times prime mode was used. (1–16 bit word);
10) Number of times stop mode was used. (1–16 bit word);
11) Serial number of SAFE console (1–16 bit word);
12) Hours of operation—can be duplicated in device embedded software in (1–16 bit word);
13) Revision of embedded software (1–16 bit word);
14) Circuit board revision (1–16 bit word);
15) Date that the treatment started—this is used to stop treatment after 24 hours. If the number of hours of use exceeds 24 hours or a day has elapsed, circuit 109 is rejected by microprocessor controller 128. (1–16 bit word); and
16) Number of times key 130 was inserted (1–16 bit word)

Information stored in key 130 can also contain data entered by the operator using the device keyboard. This information can include:
Patients age, sex and weight;
Diagnosis;
Any medication administered before and during treatment;
Blood pressure and blood gases.

At the beginning of treatment, a microprocessor controller 128 in console 110 can interrogate key 130 and determine if the shelf life of the disposable set 109 has expired. If so, microprocessor controller 128 will inform the user and will refuse to start treatment.

The model number of circuit 109 can help console 110 to setup the correct mode of treatment. For example if the set is designed for CVVH and the user attempts to initiate CVVHD treatment, microprocessor controller 128 will prevent it and inform the user. The model number can also help establish correct treatment settings. If filter 111, for example, is of pediatric size and the user attempts to set the ultrafiltrate rate to an adult value, microprocessor controller 128 will prevent the change based on the encoded filter model.

Other important checks can be performed based on the information stored in key 130. For example the software revision in microprocessor controller 128 in console 110 can be compared to the model or revision of circuit 109. An older revision of software may not support some features of a new circuit 109. Key 130 can also be used to activate different software segments included but inactive with simpler and less expensive disposables. Alternatively, key 130 can be loaded at the time of manufacturing with the software and hardware revisions that it is compatible with.

Although the present invention has been described in terms of a particular embodiment, it is not intended that the invention be limited to that embodiment. Modifications of the disclosed embodiment within the spirit of the invention will be apparent to those skilled in the art. The scope of the present invention is defined by the claims that follow.

What is claimed is:

1. A disposable cartridge for filtration of blood comprising:
   a first passage through which flows blood from and to a patient;
   a second passage through which flows filtrates removed from the blood;
   at least one blood pressure sensor; and
   a programmable memory device containing information regarding the disposable cartridge,
   wherein the information contained in the memory device relates to the manufacture of the disposable cartridge, and
   wherein the memory device information is selected from the group including serial number, model number, hardware revision and software revision of the disposable cartridge.

2. A disposable set for filtration of blood comprising:
   a first passage through which flows blood from and to a patient;
   a second passage through which flows filtrates removed from the blood;
   at least one blood pressure sensor; and
   a programmable memory device containing information regarding the disposable set,
   wherein the memory device receives information regarding a patient being treated using the disposable set, and
   wherein the information regarding the treatment of a patient is selected from the group including the date and time when the treatment started, the duration of the treatment, treatment modality, alarms, user actions, user settings including blood flow and fluid removal rate, sensor readings, and amount of fluid removed per treatment.

3. A disposable cartridge for filtration of blood comprising:
   a first passage through which flows blood from and to a patient;
   a second passage through which flows filtrates removed from the blood;
   at least one blood pressure sensor; and
   a programmable memory device containing information regarding the disposable cartridge,
   wherein the memory device receives information regarding a patient being treated using the disposable cartridge, and
   wherein the information regarding the treatment of a patient is selected from the group including the date and time when the disposable cartridge was mounted on the pump console, the date and time when the disposable cartridge was dismounted from the pump console, and battery operation.

4. A disposable cartridge for filtration of blood comprising:
   a first passage through which flows blood from and to a patient;
   a second passage through which flows filtrates removed from the blood;
   at least one blood pressure sensor; and
   a programmable memory device containing information regarding the disposable cartridge,
   wherein the information contained in the memory device relates to the operation of the disposable cartridge in connection with the treatment of a patient, and
   wherein information about the patient being treated using the disposable cartridge stored in the memory device is selected from the group including patient age, sex and weight, diagnosis, medication administered before and during treatment, and blood pressure and blood gauges.

5. A disposable cartridge for filtration of blood comprising:
   a first passage through which flows blood from and to a patient;
   a second passage through which flows filtrates removed from the blood;
   at least one blood pressure sensor; and
   a programmable memory device containing information regarding the disposable cartridge,
   wherein the memory device includes an EEPROM and is embedded in a housing of a sensor used with the disposable cartridge.

6. A disposable set for filtration of blood comprising:
   a first passage through which flows blood from and to a patient;
   a second passage through which flows filtrates removed from the blood;
   at least one blood pressure sensor; and
   a programmable memory device containing information regarding the disposable set,
   wherein the disposable set is detachably mounted on a console including at least one pump for pumping blood and a microprocessor for controlling the operation of the disposable set in combination with the console, and
   wherein the memory device is a key code card that is plugged into a control panel of the console.

7. A blood filtration system comprising:
   a filter;
   a disposable set comprising:
      a first passage through which flows blood to and from a patient,
      a second passage through which flows filtrates removed from the blood by the blood filter;
      at least one blood pressure sensor; and
      a memory device containing information regarding the disposable set; and
   a console on which the disposable set is detachably mounted for pumping the blood and the filtrates, the console including a microprocessor for controlling the operation of the disposable set in combination with the console, wherein the memory device further includes information regarding a patient being treated using the disposable set, and wherein the information regarding the treatment of a patient is selected from the group including the date and time when the treatment started, the duration of the treatment, treatment modality, alarms, user actions, user settings including blood flow and fluid removal rate, sensor readings, and amount of fluid removed per treatment.

8. A blood filtration system comprising:

a filter;

a disposable set comprising:
   a first passage through which flows blood to and from a patient,
   a second passage through which flows filtrates removed from the blood by the blood filter;
   at least one blood pressure sensor; and
   a memory device containing information regarding the disposable set; and a console on which the disposable set is detachably mounted for pumping the blood and the filtrates, the console including a microprocessor for controlling the operation of the disposable set in combination with the console, wherein the memory device further includes information regarding a patient being treated using the disposable set, and wherein the information regarding the treatment of a patient is selected from the group including the date and time when the disposable set was mounted on the pump console, the date and time when the disposable set was dismounted from the pump console, and battery operation.

9. A blood filtration system comprising:

a filter;

a disposable set comprising:
   a first passage through which flows blood to and from a patient,
   a second passage through which flows filtrates removed from the blood by the blood filter;
   at least one blood pressure sensor; and
   a memory device containing information regarding the disposable set; and a console on which the disposable set is detachably mounted for pumping the blood and the filtrates, the console including a microprocessor for controlling the operation of the disposable set in combination with the console, wherein the memory device further includes information regarding a patient being treated using the disposable set, and wherein the information about a patient being treated using the disposable set stored in the memory device is selected from the group including patient age, sex and weight, diagnosis, medication administered before and during treatment, and blood pressure and blood gauges.

10. A blood filtration system comprising:

a filter;

a disposable cartridge comprising:
   a first passage through which flows blood to and from a patient,
   a second passage through which flows filtrates removed from the blood by the blood filter;
   at least one blood pressure sensor; and
   a memory device containing information regarding the disposable cartridge; and a console on which the disposable cartridge is detachably mounted for pumping the blood and the filtrates, the console including a microprocessor for controlling the operation of the disposable cartridge in combination with the console, wherein the memory device includes an EEPROM and is embedded in a housing of a sensor used with the disposable cartridge.

11. A blood filtration system comprising:

a filter;

a disposable set comprising:
   a first passage through which flows blood to and from a patient,
   a second passage through which flows filtrates removed from the blood by the blood filter;
   at least one blood pressure sensor; and
   a memory device containing information regarding the disposable set; and a console on which the disposable set is detachably mounted for pumping the blood and the filtrates, the console including a microprocessor for controlling the operation of the disposable set in combination with the console, wherein the memory device is a key code card that is plugged into a control panel of the console.

* * * * *